United States Patent [19]
Loge

[11] Patent Number: 5,991,020
[45] Date of Patent: *Nov. 23, 1999

[54] METHOD FOR DETERMINING THE CONCENTRATION OF ATOMIC SPECIES IN GASES AND SOLIDS

[76] Inventor: Gary W. Loge, 2998 Plaza Blanca, Santa Fe, N.Mex. 87505

[*] Notice: This patent is subject to a terminal disclaimer.

[21] Appl. No.: 09/018,105

[22] Filed: Feb. 3, 1998

Related U.S. Application Data

[63] Continuation-in-part of application No. 08/553,761, Oct. 23, 1995, Pat. No. 5,715,053.

[51] Int. Cl.[6] ............................. G01N 21/73; G01N 21/63
[52] U.S. Cl. ............................. 356/316; 356/318
[58] Field of Search ..................... 356/316, 317, 356/318

[56] References Cited

U.S. PATENT DOCUMENTS

| | | | |
|---|---|---|---|
| 5,446,538 | 8/1995 | Noll | 356/318 |
| 5,715,053 | 2/1998 | Loge | 356/318 |

Primary Examiner—F. L. Evans
Attorney, Agent, or Firm—Samuel M. Freund

[57] ABSTRACT

Method for determining the concentration of atomic species in gases and solids. Measurement of at least two emission intensities from a species in a plasma containing the species after a sufficient time period has elapsed after the generation of the plasma and during a second time period, permits an instantaneous temperature to be established within the sample. The concentration of the atomic species to be determined is then derived from the known emission intensity of a predetermined concentration of that species in the sample at the measured temperature, a quantity which is measured prior to the determination of the unknown concentration, and the actual measured emission from the unknown species, or by this latter emission and the emission intensity of a species having known concentration within the sample.

12 Claims, 3 Drawing Sheets

METHOD FOR DETERMINING THE CONCENTRATION OF ATOMIC SPECIES IN GASES AND SOLIDS

This application is a continuation-in-part of application Ser. No. 08/553,761 filed on Oct. 23, 1995, now U.S. Pat. No. 5,715,053.

The invention was made with government support under DOE grant No. DE-FG02-94ER81671 awarded by the U.S. Department of Energy to Laser Diagnostics L.L.C., a New Mexico Company. The government has certain rights in the invention.

FIELD OF THE INVENTION

The present invention relates generally to spectroscopic determination of the concentration of atomic species in samples and, more particularly, to the use of a pulsed or continuous plasma source from which atomic species present may be quantitatively determined from their emission spectra with corrections for changing plasma characteristic, and detection efficiency.

BACKGROUND OF THE INVENTION

The laser spark has been used as an excitation source for the in situ analysis of gases, solids, aerosols, and liquids by atomic emission spectroscopy. A powerful laser pulse is focused onto or into the material to be analyzed, thereby vaporizing the material and forming a plasma having high temperature and electron density. By spectrally analyzing light emitted from electronically excited species, one can identify these species.

One problem with this method is that the spark volume and density, and the ultimate temperature of the plasma may vary as a result of sample and laser conditions making quantitative analysis unreliable. Sample conditions that can affect the spark volume and density, and the plasma temperature include the presence of easily ionizable elements such as sodium, the amount of water content, atmospheric pressure, the size and density of microscopic particles and condensed water droplets in gas samples, and the granule size of solid samples, most of which can vary between laser pulses. In addition, the laser pulse energy can vary, which affects the spark size and temperature between pulses.

Another problem with this technique when used for quantitative analysis is a change in the detector efficiency. This can result from drifting optical alignment causing the laser focus to move outside the detector field-of-view, or from deteriorating collection optics causing less light to reach the detector. Both a pulse-to-pulse variation in spark volume and a drift in detector efficiency will cause the intensity of the entire emission spectrum to change, but on different time scales.

Yet another problem with using LIBS for quantitative analysis that has not been considered is that changes in plasma temperature with constant species concentration will cause the laser spark emission intensity and the distribution of intensity among atomic emission lines to change because of changes in the population of higher energy atomic levels. The relationship between spark temperature and the degree of excitation was noticed by Joseph R. Wachter and David A. Cremers in "Determination of Uranium in Solution Using Laser-Induced Breakdown Spectroscopy," Applied Spectroscopy 41, 1041 (1987). Therein, the authors noted that the temperature and electron density of a laser spark in water were found to be 8000 K and $9 \times 10^{17}$ cm$^{-3}$, respectively, 1 µs after plasma formation, whereas the same quantities for a spark in air were found to be 17,000 K and $2 \times 10^{17}$ cm$^{-3}$, and speculated that the spark temperature is likely to be lower in liquids because a large fraction of the laser pulse energy goes into vaporization of the liquid, leaving a smaller fraction for plasma formation, when compared with that for the spark in air. Similar problems exist for the application of other plasma sources to the analysis of gas and solid samples with varying characteristics. For example, a pulsed, electrical discharge spark will have problems of changing plasma temperature and spark volume as sample characteristics change. For continuous plasma sources, such as Inductively-Coupled Plasmas (ICPs) and Microwave-induced Plasmas (MIPs), the steady-state plasma temperature will vary as conditions change, rather than changing between pulses.

The above-described problems may be compensated for in part by introducing known standards into the plasma to calibrate the system. See, e.g., "Detector For Trace Element Analysis Of Solid Environmental Samples By Laser Plasma Spectroscopy, by Richard Wisbrun et al., Anal. Chem. 66, 2964 (1994), where different classes of soil samples containing known amounts of metals were used as calibration standards, and "Metal-Pollution Monitor Passes Field Test," Laser Focus, February 1995, page 16, where it was proposed to introduce certain metals of interest into the waste stream of a smokestack at known levels and monitor the LIBS signals. However, such introduction is generally difficult and unreliable for flowing gases, and sample conditions often change after a calibration is performed both for solids and gases. For quantitative analysis in the laboratory, where gas or other sample characteristics are tightly controlled, calibration does not change and, consequently, the method of using standards in the plasma to calibrate the system works well. Such is not true when attempting quantitative analysis in the field.

Mention has been made of the determination of the temperature for a plasma in thermodynamic equilibrium using the two-line Boltzman method in "Detection of Cadmium, Lead and Zinc in Aerosols by Laser-Induced Breakdown Spectrometry," by Marcelino Essien, Leon J. Radziemski and Joseph Sneddon, J. Anal. Atomic Spectrometry 3, 985 (1988). Therein, it was stated that there is evidence that the laser-induced plasma is in local equilibrium about 1 µs after the onset of plasma formation. Small changes in the laser output and optical alignment were compensated for by the authors by expressing the signal as a ratio of the intensity of the analyte line to the adjacent background. No suggestion or discussion is to be found therein for using the plasma temperature concentration measurements for changing conditions. See also, "Temperature Measurement From First-Negative N$_{2+}$Spectra Produced By Laser-Induced Multiphoton Ionization And Optical Breakdown Of Nitrogen," by Christian Parigger et al., Applied Optics 18, 3331 (1995), and "Electron Number Density And Temperature Measurement In A Laser-Induced Hydrogen Plasma," by Christian Parigger et al., J. Quant. Spectrosc. Radiat. Transfer 53, 249 (1995), for temperature measurements in plasmas. No suggestion or discussion is to be found therein for correcting measurements of line intensities of other species in the plasmas for the plasma temperature during the measurement or for measuring absolute concentrations. For microwave induced plasmas, it is well known that the electron temperature is different from the statistical temperature of the atomic and ionic energy levels. However, this statistical temperature can still be used, since it is that which affects the atomic and ionic emission intensity from specific energy levels. Additionally, a recently published discussion of the "excitation temperature," that is, the electron temperature versus the equilibrium temperature may result in errors in some cases, but not in all cases. See, "Determination Of The Excitation Temperature In A Nonthermodynamic-Equilibrium High-Pressure Helium Microwave Plasma Torch," by M. C. Quintero et al., Appl. Spectro. 51, 778 (1997).

Accordingly, it is an object of the present invention to provide a method for quantitatively determining the concentration of atomic species in gases or solids using a plasma without the uncertainties introduced by variations in temperature and other plasma characteristics.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the method for determining the concentration of selected atomic species in a sample hereof includes the steps of generating a plasma in or on the surface of the sample from which light is emitted; obtaining a wavelength-resolved optical spectrum from the light emitted from the plasma over a chosen wavelength range which, for a pulsed plasma source, will be time resolved beginning a chosen time after the generation of the plasma and continuing for a chosen time interval thereafter, such that the obtained spectrum substantially represents thermally-equilibrated species at an instantaneous temperature within the plasma; calculating the plasma temperature from the measured emission intensity from an atomic or molecular species in the sample using at least two emission lines therefrom from different excited-states and within the chosen wavelength range; measuring the emission intensity from the selected atomic species using at least one emission line within the chosen wavelength range having known line strength; and normalizing the measured emission intensity of the selected atomic species using the calculated temperature to determine the relative population of the atomic level which gave rise to the emission line intensity.

It is preferred that the method hereof further includes the step of normalizing the measured emission intensity of the selected atomic species with the measured emission intensity of an atomic or molecular species having a known concentration to correct for variations in sample conditions or in optical alignment.

It is also preferred that the atomic or molecular species having known concentration includes nitrogen already present in atmospheric gas samples when a laser spark is used to generate the plasma.

Preferably the method includes the steps of measuring a substantial portion of the light emitted from the plasma, and normalizing the emission intensity from the selected atomic species with the light emitted from the plasma in order to correct for variations in sample conditions.

Benefits and advantages of the invention include rapid and reliable concentration determinations that are corrected for changing conditions without performing a recalibration.

BRIEF DESCRIPTION OF THE DRAWINGS

The accompanying drawings, which are incorporated in and form a part of the specification, illustrate an embodiment of the present invention and, together with the description, serve to explain the principles of the invention.

DETAILED DESCRIPTION OF A PREFERRED EMBODIMENT OF THE INVENTION

Briefly, the present invention includes a method for calibrating emission lines from atomic species to be quantitatively determined and/or monitored in samples in which a plasma containing the emitting species has been generated. The novel aspect is normalization involving determination of the instantaneous plasma temperature. This may be achieved by utilizing at least two emission lines of the species whose concentration is to be determined, or at least two emission lines from another species present in the sample. An additional correction for changes in sample or plasma source conditions or detector efficiency or alignment may be made using a known quantity of a species in the unknown sample or by using a calibration sample containing a known amount of the species to be determined in the unknown sample. Another way to perform the additional correction for changes in sample or laser conditions is to measure a substantial portion of the emitted light from the plasma and normalize subsequently measured emitted light intensity to that emitted using a known sample.

Figure 1A:
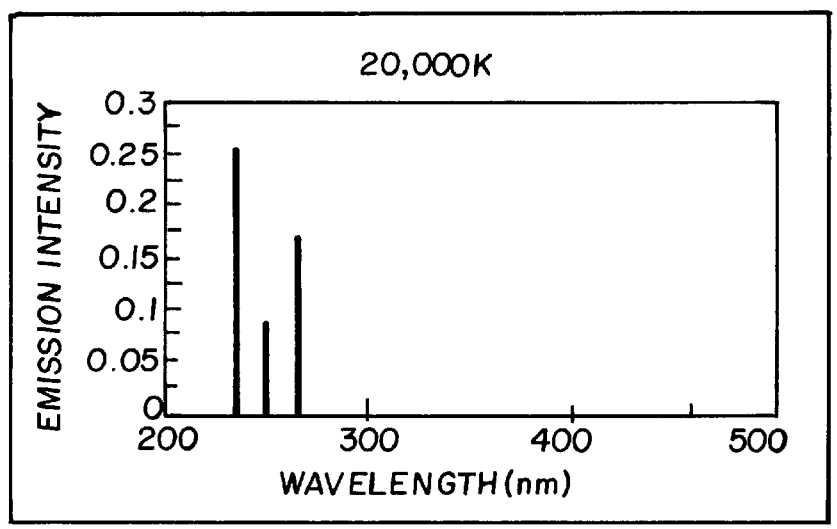
FIGS. 1a–c are simulated laser spark emission spectra for beryllium at three plasma temperatures, showing a change in relative intensity of the emission lines as the temperature is changed. Note that the emission intensity scales are different for the three Figures.
Figure 1B:
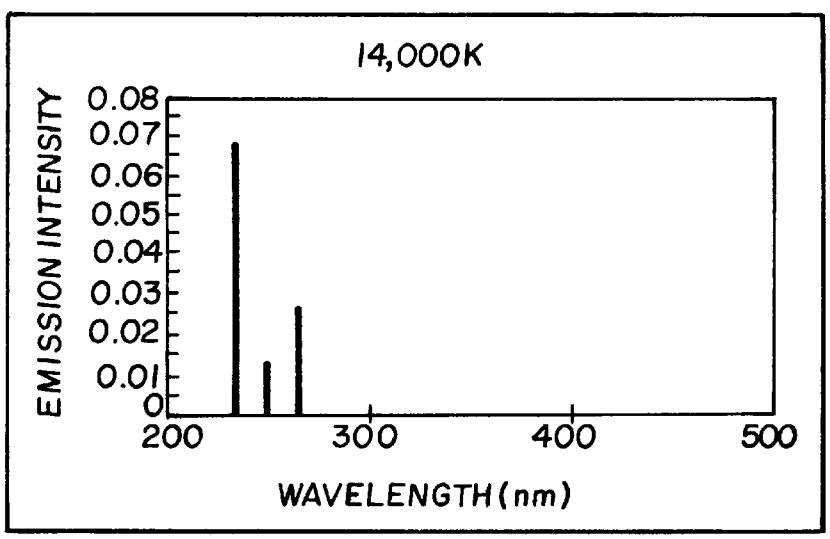
Figure 1C:
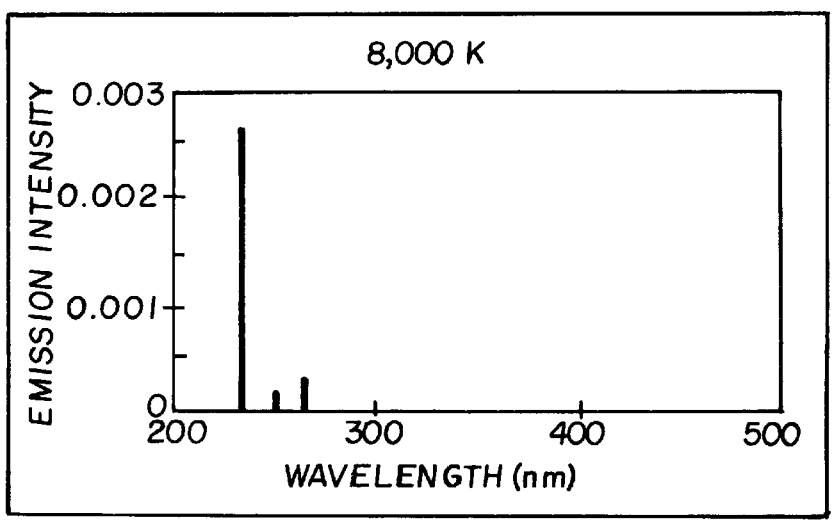

Reference will now be made in detail to the present preferred embodiments of the invention, examples of which are illustrated in the accompanying drawings. Turning now to the drawings, FIGS. 1a–c show simulated plasma emission spectra for beryllium at three plasma temperatures, and illustrate the change in relative intensity of the emission lines as the temperature is changed. Note that the emission intensity scales are different for the three Figures. Simulated emission spectra calculations were generated for a constant number density of ground-state beryllium atoms which is approximately the same as the total atomic number density—except for a small fraction of atoms in excited-states. However, it is this small fraction of atoms in excited-states that varies significantly with temperature and gives rise to the substantially different emission spectra observed.

To generate FIG. 1a–c, relative upper-state populations were obtained using a thermal statistical population distribution, $Q_i(T)$, and atomic line strengths, $S_{ij}$, which were obtained from "Wavelengths and Transition Probabilities for Atoms and Atomic Ions-Part II. Transition Probabilities," by W. L. Weise and G. A. Martin, NTIS Publication No. PB81-206120, pages 359 ff. (December 1980). A change in the relative intensity of emission lines with temperature within the spectrum of a species may readily be seen. The effect derives from the changing population in the excited-state levels with temperature.

As stated, the three most important factors leading to inaccurate measurements in plasma spectroscopic investigations are variations in the temperature of the electron, the plasma density, and the actual plasma volume in the detector field-of-view. An emission line intensity may be expressed as a function of temperature as follows:

$$I(T)=aVSij[X]Qi(T) \qquad \text{Eq. 1,}$$

where a is the emitted light collection and detection efficiency of the apparatus which is constant for a fixed optical geometry and detector-except for wavelength sensitivity and degradation of optical quality, V is proportional to the total plasma volume contained in the detector field-of-view and the plasma density which may vary for gas samples as a result of dust particles or other changing gas conditions, although not as much where solids are to be investigated under more controlled conditions, Sij is the emission probability for the transition from level "i" to level "j" of the emitting species, which is a constant for a specific emission feature, [X] is the number density of "X" atoms in the sample, which is the quantity to be measured, and Qi(T) is the fraction of "X" atoms in the upper-state emitting level, which is a known function of temperature and electron density. By measuring I(T) for at least two emission features originating from different excited-state levels of a species in the sample, which may be the species to be quantitatively determined or monitored or may be another species present in the sample, within a short time period for pulsed plasma sources, the instantaneous temperature for pulsed plasma sources or steady-state temperature for continuous plasma sources of the gas may be readily determined from Eq. 1. It should be mentioned that the time required for localized thermal equilibrium to occur in pulsed plasmas has been previously shown to be of the order of 1 $\mu$s (see, e.g., Essien et al., supra), while the time period for significant subsequent temperature change in the plasma is expected to be about 1 $\mu$s as well. Therefore, emission line intensity measurements should be conducted between about 1 and 2 $\mu$s for a typical pulsed spectroscopic measurement.

If a known concentration of an internal standard, $X_k$, such as nitrogen is present (See, e.g., the Parigger et al. references, supra), the intensity $I_k(T)$ may be measured for this species (species "$X_k$") at the temperature determined using Eq. 1 by measuring at least one emission feature thereof, from which $$aV=I_k(T)/S[X_k]Qik(T) \qquad \text{Eq. 2,}$$

and is determined under the same conditions that the measurement of the species of interest is to be taken. All parameters are then known at the instantaneous or steady-state plasma temperature, and changes in the characteristics of the plasma source or drift in optical alignment or conditions, may be compensated for. It should be mentioned that nitrogen can only be used as an internal standard according to the method of the present invention if the plasma is generated using a laser spark, since only then will significant quantities of atomic nitrogen be generated.

Another way to compensate for variations in plasma spark intensity which avoids continuous use of an internal standard, $X_k$, is to measure a substantial portion of the light emitted from the plasma, and normalize emission intensities by this quantity. Although this procedure is clearly not as accurate as the on-line measurement using an internal standard, it is of significant assistance in many situations.

Figure 2:
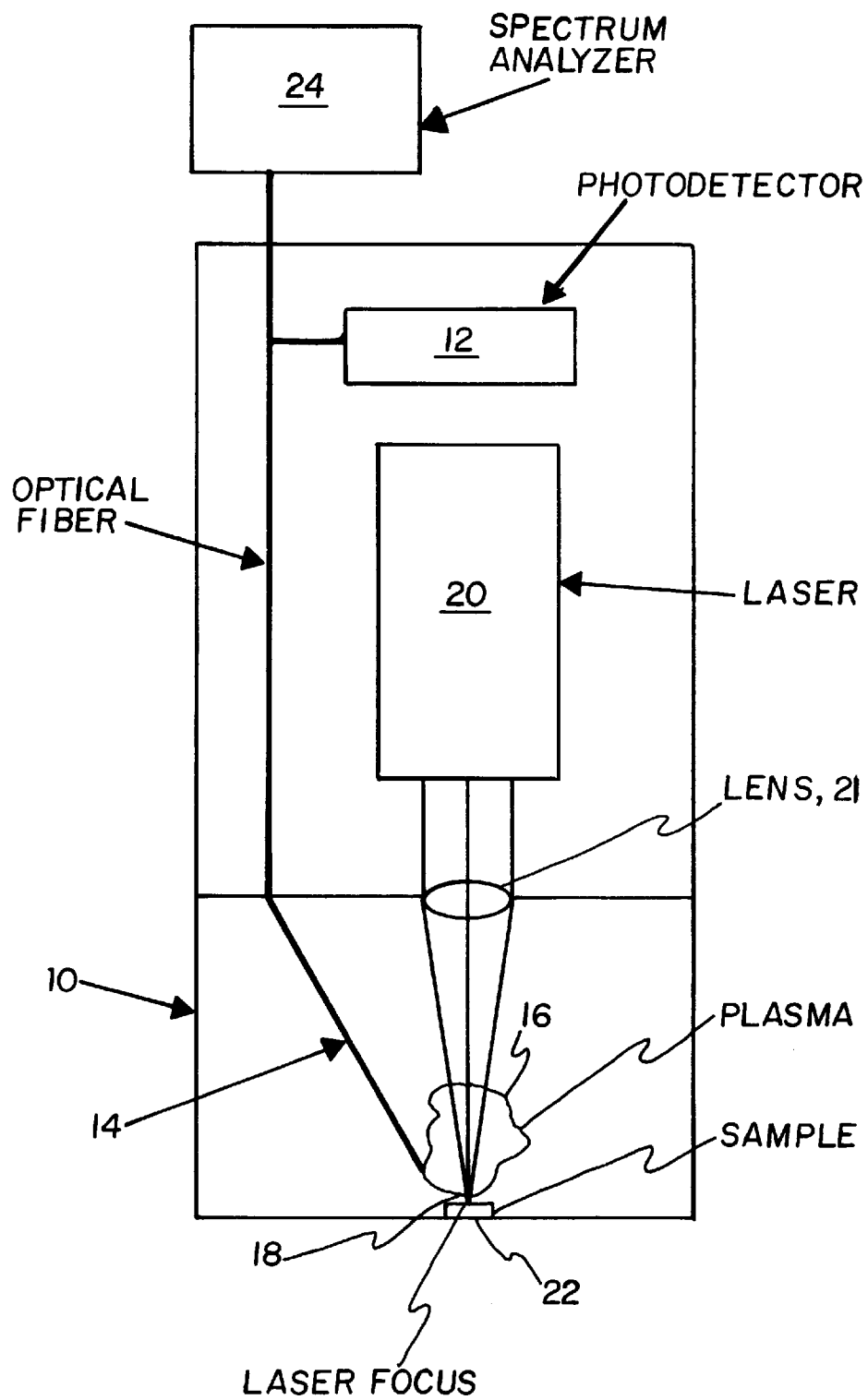
FIG. 2 is a schematic representation of one possible apparatus used to practice the method hereof, showing a photodetector positioned such that a measurement of the emission intensity of a laser-induced plasma may be made in order to correct for changes in plasma characteristics other than the temperature between an unknown sample and previously obtained calibration standard samples while using a mechanically rigid geometry for the laser generated plasma source and detector field-of-view.
Figure 3:
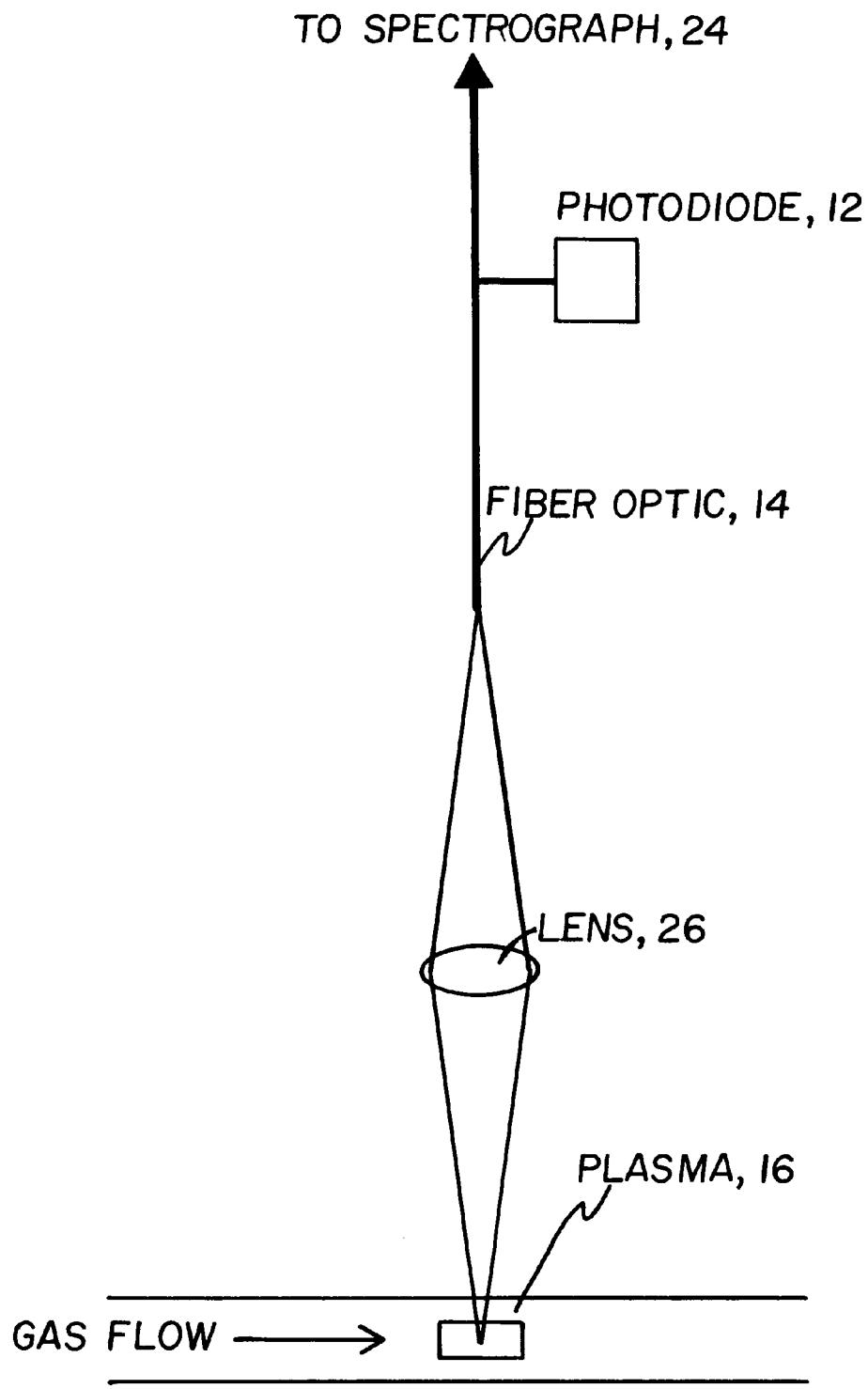
FIG. 3 is a schematic representation of an apparatus suitable for practicing the method of the present invention when a plasma source other than a laser-generated plasma source is employed.

FIG. 2 is a schematic representation of an apparatus, 10, which may be used to practice the method hereof, showing a photodetector, 12, and optical fiber, 14, positioned such that a substantial portion of the emission from the plasma, 16, may be measured in order to correct for changes in plasma characteristics over time. For a fixed "a" (one where laser focus, 18, generated by laser, 20, and lens, 21, on sample, 22, and optic fiber, 14, are spatially fixed relative to one another), a separate calibration, using a known species in the sample, may be used to determine "aV". Photodetector, 12, may then be used to normalize the emission intensity for each laser pulse, in order to correct for changes in "V" for an unknown sample. Shown in FIG. 2 is optical fiber, 14, that is also used for directing a portion of the light from plasma, 16, into spectrum analyzer, 24, which measures the line intensities for individual emission lines therein in a chosen spectral region. FIG. 3 is a schematic representation of a more general apparatus for practicing the method of the present invention, where the plasma is generated in the sample by other means than a laser spark. Similar structure to that of FIG. 2 hereof is identified using identical callouts. Lens, 26, is employed to couple light from plasma 16 into fiber optic 14.

The foregoing description of the preferred embodiments of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining the concentration of a first atomic species in a sample, which comprises the steps of:
    a. generating a plasma in or on the surface of the sample from which light is emitted;
    b. obtaining a wavelength-resolved optical spectrum from the light emitted from the plasma over a chosen wavelength range which, for a pulsed plasma source, will be time resolved beginning a chosen time after generation of the plasma and continuing for a chosen time interval thereafter, such that the obtained spectrum substantially represents thermally-equilibrated species at an instantaneous or steady-stated temperature within the plasma;
    c. calculating the instantaneous or steady-state plasma temperature using the measured emission intensity from a second species in the sample using at least two emission lines therefrom within the chosen range of wavelengths;
    d. measuring the emission intensity from the first atomic species using at least one emission line within the chosen wavelength range and having a known line strength; and
    e. normalizing the measured emission from the first atomic species using the relative population of the atomic level that gave rise to the emission line intensity which is calculated from the instantaneous or steady-state temperature.

2. The method for determining the concentration of a selected atomic species in a sample, as described in claim 1, further comprising the step of normalizing the measured emission intensity of the at least one emission line of the first atomic species with the emission intensity of the second species, wherein the second species has known concentration therein, in order to correct for changes in measured intensity from the first atomic species resulting from variations in sample conditions and detector alignment.

3. The method for determining the concentration of a first atomic species in a gaseous sample as described in claim 1, wherein the chosen time is greater than approximately 1 $\mu$s, and the chosen time interval is less than approximately 1 $\mu$s.

4. A method for determining the concentration of a first atomic species in a sample, which comprises the steps of:
   a. generating a plasma in or on the surface of the sample from which light is emitted;
   b. obtaining a wavelength-resolved optical spectrum from the light emitted from the plasma over a chosen wavelength range which, for a pulsed plasma source, will be time resolved beginning a chosen time after generation of the plasma and continuing for a chosen time interval thereafter, such that the obtained spectrum substantially represents thermally-equilibrated species at an instantaneous or steady-state temperature within the plasma;
   c. calculating the instantaneous or steady-state plasma temperature using the measured emission intensity from the first atomic species in the sample using at least two emission lines thereof within the chosen range of wavelengths;
   d. normalizing the measured emission intensity from the at least two emission lines of the first atomic species using the relative population of the atomic levels that gave rise to the emission line intensity which is calculated from the instantaneous or steady-state temperature;
   e. measuring the emission intensity from a second species in the sample having a known concentration therein, using at least one emission line thereof within the chosen wavelength range; and
   f. normalizing the measured emission intensity from the first atomic species with the emission intensity for the second species at the instantaneous or steady-state plasma temperature, in order to correct for changes in emission intensity from the first atomic species resulting from variations in sample conditions and detector alignment.

5. The method for determining the concentration of atomic species in a sample as described in claim 4, wherein the chosen time is greater than approximately 1 $\mu$s, and the chosen time interval is less than approximately 1 $\mu$s.

6. A method for determining the concentration of a first atomic species in a sample, which comprises the steps of:
   a. generating a plasma in or on the surface of the sample from which light is emitted;
   b. obtaining a wavelength-resolved optical spectrum from the light emitted from the plasma over a chosen wavelength range which, for a pulsed plasma source, will be time resolved beginning a chosen time after the generation of the plasma and continuing for a chosen time interval thereafter, such that the obtained spectrum substantially represents thermally-equilibrated species at an instantaneous or steady-state temperature within the plasma;
   c. calculating the instantaneous or steady-state plasma temperature from the measured emission intensity from a species in the sample using at least two emission lines therefrom within the chosen wavelength range;
   d. measuring the emission intensity from the first atomic species using at least one emission line within the chosen wavelength range and having a known line strength; and
   e. normalizing the measured emission intensity from the at least one emission line of the first atomic species using the relative population of the atomic level that gave rise to the emission line intensity which is calculated from the instantaneous or steady-state temperature.

7. The method for determining the concentration of a first atomic species in a sample as described in claim 6, wherein the species used for determination of the temperature is the first atomic species.

8. The method for determining the concentration of a first atomic species in a sample as described in claim 6, wherein the species used for determination of the temperature is other than the first atomic species.

9. The method for determining the concentration of atomic species in a sample as described in claim 6, wherein the chosen time is greater than approximately 1 $\mu$s, and the chosen time interval is less than approximately 1 $\mu$s.

10. The method for determining the concentration of a first atomic species in a sample, as described in claim 6, further comprising the step of calibrating the measured emission intensity using the measured emission intensity of a species present in a known concentration in a calibration sample, similar to the unknown sample, in order to correct for changes in measured intensity from the first atomic species resulting from variations in sample conditions and detector alignment.

11. The method for determining the concentration of a first atomic species in a sample as described in claim 10, wherein the species is the first species introduced into the sample at a known concentration.

12. The method for determining the concentration of atomic species in a sample as described in claim 10, further comprising the steps of measuring a substantial portion of the light emitted from the plasma, and normalizing the emission intensity from the first atomic species with the light emitted from the plasma from both the calibration and unknown samples in order to correct for variations in sample conditions and detector alignment.

* * * * *